United States Patent [19]

Hägerdal et al.

[11] Patent Number: 4,524,137

[45] Date of Patent: Jun. 18, 1985

[54] PREPARATION OF CATALYSTS FOR BIOCHEMICAL CONVERSION REACTIONS

[76] Inventors: Bärbel G. R. Hägerdal, Mätaregränden 10, S-222 47 Lund; Klaus H. Mosbach, Lackalänga 31-38, S-244 02 Furulund, both of Sweden

[21] Appl. No.: 261,220

[22] PCT Filed: Aug. 22, 1980

[86] PCT No.: PCT/SE80/00216

§ 371 Date: Apr. 13, 1981

§ 102(e) Date: Apr. 13, 1981

[87] PCT Pub. No.: WO81/00576

PCT Pub. Date: Mar. 5, 1981

[30] Foreign Application Priority Data

Aug. 23, 1979 [SE] Sweden ............................ 7907035

[51] Int. Cl.$^3$ ..................... C12N 11/10; C12N 11/08; C12P 7/14
[52] U.S. Cl. .................................. 435/178; 435/161; 435/162; 435/179; 435/180; 435/182
[58] Field of Search .............. 435/174, 175, 177, 178, 435/182, 161, 162

[56] References Cited

U.S. PATENT DOCUMENTS

| | | | |
|---|---|---|---|
| 3,616,229 | 10/1971 | Wildi et al. ........................ | 435/175 |
| 3,836,433 | 9/1974 | Wirth et al. ..................... | 435/178 X |
| 3,841,971 | 10/1974 | Messing .............................. | 435/175 |
| 3,950,222 | 4/1976 | Takasaki .............................. | 435/174 |
| 3,990,944 | 11/1976 | Gauss et al. ........................ | 435/162 |
| 4,177,107 | 12/1979 | Kumakura et al. ................. | 435/176 |
| 4,245,064 | 1/1981 | Drobnik et al. ................. | 435/178 X |

FOREIGN PATENT DOCUMENTS 2703834 1/1977 Fed. Rep. of Germany .
1115011 5/1968 United Kingdom .

OTHER PUBLICATIONS

Kierstan, M. et al., "The Immobilization of Microbial Cells, Subcellular Organelles, and Enzymes in Calcium Alginate Gels", Biotech. & Bioeng., vol. XIX, 1977, (pp. 387–397).

Hagerdal et al., The Direct Conversion of Cellobiose to Ethanol Using Bakers Yeast Co-Immobilized with Beta-Glucosidase, 27th IUPAC Congress, Helsinki, 1979, (p. 545).

Vieth, W. R. et al., "Enzyme Engineering Part II. Materials for Immobilized Enzyme Reactors", Chemtech, Jan. 1974, pp. 47–55.

Nilsson, H. et al., "The Use of Bead Polymerization of Acrylic Monomers for Immobilization of Enzymes", Biochim. Biophys. Acta, 268, pp. 253–256, (1972).

Hagerdal, B., "Ethanol Produced from Whey Permeate in a Reactor Composed of Co-Immobilized Lactase and Bakers Yeast Cells", Demonstration and Poster Paper Abstracts, Chemical Center, Lund, Nordforsk Seminar, May 13, 1980, No. 16.

Primary Examiner—David M. Naff
Attorney, Agent, or Firm—Browdy and Neimark

[57] ABSTRACT

A catalyst is disclosed, which can be used for carrying out, in a continuous manner simultaneously and in one and the same reaction space, two or more stages of a biochemical conversion reaction which is of the kind requiring, for certain reaction stages, the presence of an enzyme, and for other reaction stages the presence of a microorganism. The catalyst comprises solid bodies of one or more polymers of which at least one is a cross-linked polymer. At least one enzyme is bound to the polymer material of the solid bodies by covalent bonds, and at least one microorganism is physically entrapped in the three-dimensional structure of the cross-linked polymer of the solid bodies.

9 Claims, 1 Drawing Figure

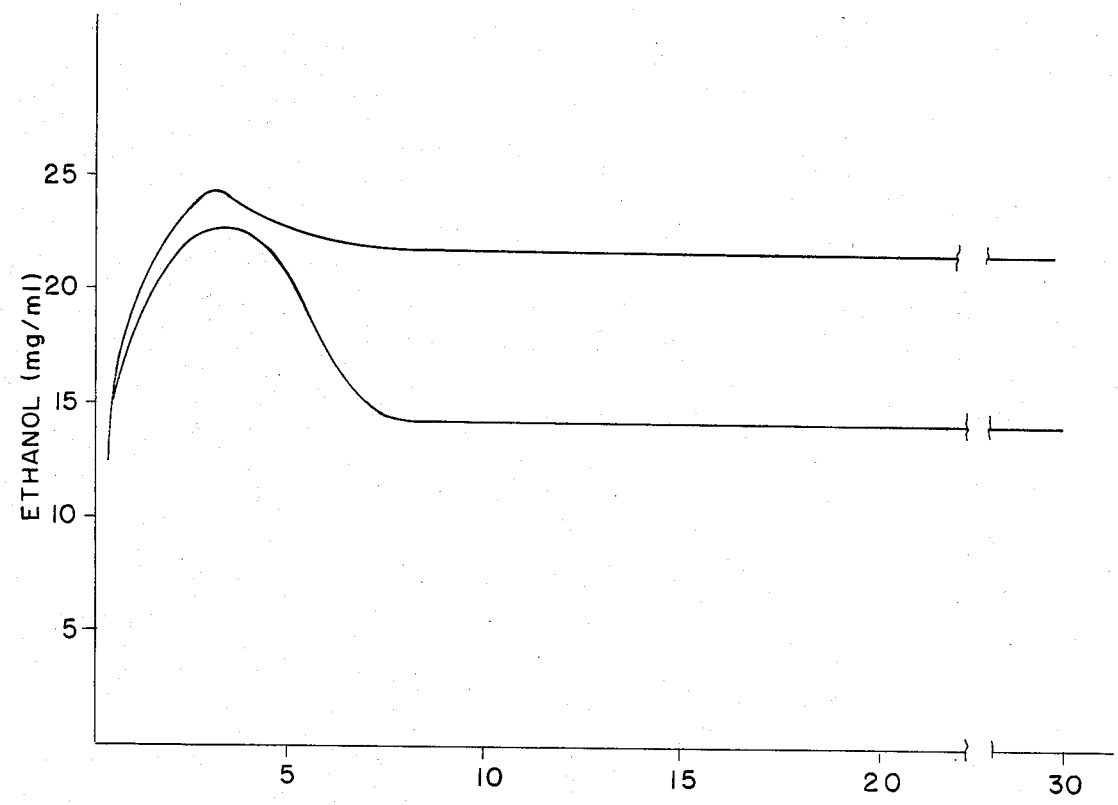

PREPARATION OF CATALYSTS FOR BIOCHEMICAL CONVERSION REACTIONS

The present invention relates to a catalyst for biochemical conversion reactions of the kind which proceed in two or more stages from a substrate or a substrate mixture to a desired end product via one or more intermediate products, whereat certain of the conversion stages require the presence of one or more enzymes, while others of said stages require the presence of one or more microorganisms.

The invention also relates to a method of manufacturing such a catalyst.

A very large number of different biochemical conversion reactions are known which in principle proceed in the form of a chain of a plurality of sequential reaction stages, and which require the presence of enzymes in certain of the reaction stages and the presence of microorganisms in other stages. These biochemical conversion reactions are thus, in principle, of the kind

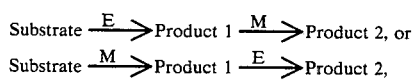

where E represents one or more enzymes and M represents one or more microorganisms. As will be understood, the reaction chain may often comprise more than two stages.

Examples of conversion reactions of the first kind include

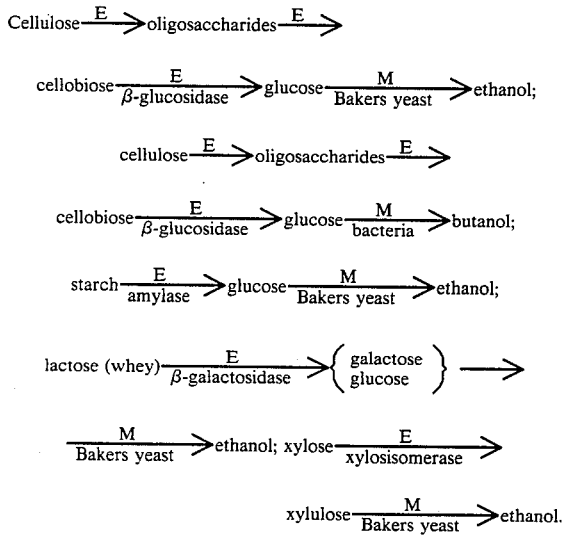

One example of the other type of conversion reaction is

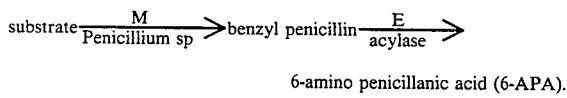

6-amino penicillanic acid (6-APA).

These are only a very few examples of the large number of biochemical conversion reactions known to the art.

One characteristic of these biochemical reactions is that the reaction rate is influenced by the presence of the product formed, in a manner such as to cause the reaction to proceed progressively slower, and to finally stop altogether when the content of the formed product increases. When carrying out the various reaction stages in the process batchwise, the reaction will thus stop automatically at relatively low yield, whereafter it is necessary to separate the formed product from the substrate and the catalyst used, i.e. the enzyme or microorganism used, so that the catalyst, which is often expensive, can be used again. Neither should the catalyst be present in the final product removed, since such presence is often undesirable. These separation operations, however, are often complicated and expensive to carry out. Consequently, it is desirable that the various stages in such a process can be carried out by means of a continuous method in which the reaction products are continuously removed from the reaction space, to allow the reaction to proceed without hinder, thereby to provide a high yield. Such a continuous process, however, requires the catalyst used, i.e. the enzyme or the microorganism used, to be immobilized in one way or another, so that said catalyst does not accompany the continuous flow of reaction products from the reaction space, but remains in said space. Further, it would be to great advantage, both economically and practically, if it were possible to carry out two or more of the stages in a biochemical conversion reaction of the kind in question in one and the same reaction chamber, e.g. in one and the same column. This requires, however, the simultaneous presence in the reaction chamber of the enzymes and microorganisms necessary for the various stages, and said enzymes and microorganisms to be in an immobilized state in the reaction chamber. Certain processes have been proposed in which both an enzyme and a microorganism are present in the reaction chamber at the same time, for simultaneously carrying out two mutually different stages in a biochemical conversion reaction. Since in this cases, however, one has been concerned with batchwise processes, only low yields have been obtained, and it has been necessary upon completion of the reaction to try to separate the enzyme and the microorganism used from the reaction products. For the purpose of carrying out the various reaction stages continuously, methods of immobilizing each of the enzymes and microorganisms per se in mutually different kinds of carriers have also been proposed. One serious problem encountered when immobilizing enzymes is that enzymes have a relatively small molecular size, and hence they cannot readily be immobilized solely by adsorption or by entrapping them purely physically in a carrier. This results in a substantial loss or "leakage" of the enzyme from the carrier, thereby causing the activity to decrease rapidly and the enzyme catalyst to lose its effect, whereupon the catalyst must be changed. Further, in order for various, mutually different reaction stages in a biochemical conversion process to be carried out at the same time effectively in one and the same reaction space, it is necessary that the product formed in a preceding reaction stage, e.g. under the action of an enzyme, is brought into contact with the enzyme or the microorganism required for the next-following reaction stage as quickly and as effectively as possible. This would appear difficult to achieve, if the requisite enzymes and microorganisms are immobilized per se in mutually different carriers.

An object of the invention is therefore to provide a novel and efficient catalyst which can be used for carrying out continuously in one and the same reaction space two or more different stages of a biochemical conversion reaction which requires, for certain reaction stages, the presence of at least one enzyme, and for other reaction stages the presence of at least one microorganism.

This object is achieved by means of a catalyst according to the invention, which is mainly characterized in that said catalyst comprises solid carrier bodies of one or more polymers, of which at least one is a cross-linked polymer, and in that at least one enzyme is bound to the polymer material of the carrier bodies by covalent bonds, and that one microorganism is physically entrapped in the three-dimensional space network of said bodies.

Because the microorganism is bound to the polymer material of the carrier bodies by covalent bonds, the loss, or "leakage", of the enzyme from said bodies during the course of the reaction is very small, whereby the catalyst obtains a long useful life. The microorganisms are of such molecular size as to enable them to be held effectively to the carrier bodies without difficulty, owing to the fact that they are physically entrapped in the three-dimensional lattice formed by the cross-linked polymer of the carrier bodies. Because both the enzyme and microorganism are bound in one and the same carrier bodies, the enzyme and microorganism will be very close to each other spacewise, thereby enabling the various steps of the conversion reaction process to take place very rapidly, one after the other, which has been found to produce high yields.

In principle a catalyst according to the invention can be produced in the following manner:

An enzyme is added to a polymer or monomer in solution or suspension, subsequent to previously activating suitable binding groups of either the polymer or monomer respectively, or the enzyme, so that when the polymer, or monomer, and the enzyme are brought together, the enzyme is bound to the molecules of the polymer or monomer by covalent bonds. There is then added to the resultant suspension or solution of polymer, or monomer, with the covalently bound enzyme, a further polymer or monomer, which may be the same as or different than the first polymer or monomer used, but which is capable of cross-linking, and also a microorganism, whereafter the system is subjected to a cross-linking process, so as to obtain solid bodies of a three-dimensional cross-linked polymer, in which the enzyme is bound to the polymer material by covalent bonds and the microorganism is physically entrapped in the three-dimensional structure of the cross-linked polymer.

Two possibilities are conceivable in such manufacture of a catalyst according to the invention. One possibility is that the "apparent" molecular size of the enzyme is so "enlarged", as a result of being bound to the first polymer by covalent bonds, that these polymer-enzyme aggregates can readily be entrapped in and held within the three-dimensional network of the subsequently formed cross-linked polymer, in the same manner as the microorganism. The other possibility is that the polymer, or monomer, with the enzyme covalently bound thereto is incorporated as an integral part in the structure of the subsequently prepared cross-linked polymer.

Several different chemical groups in the molecules of the enzyme or polymer, or monomer, can be used for establishing the covalent bonds between enzyme and polymer, or monomer. These groups include, for example, hydroxyl groups, carboxyl groups, phenyl groups, tyrosine groups, amino groups, and thiol groups. All of these activatable groups are normally found in the enzyme, while the polymer, or monomer, normally has only one or two activatable molecular groups. Activation of the bonding groups used can either take place on the enzyme or on the polymer, or monomer. Preferably it is the polymer, or monomer, which is activated, since the enzyme is, in many cases, of a kind which can be deleteriously affected by the activating reaction. The covalent bonds between enzyme and polymer, or monomer, can be reversible or irreversible.

Various different activating reactions can be used for activating the aforementioned activatable groups. Examples of such reactions include acylation, arylation, alkylation, cyanogen-bromide activation, carbamylation, thiocarbamylation, amidination, reactions with polymeric aldehydes, glutaraldehyde reactions, diazotization, thioldisulphide-exchange reactions, and four-component condensation reactions. Such activation reactions for creating covalent bonds between different molecules are well known.

The method of the invention can be carried out with the use of many different polymers. Examples of polymers which can be used include polysaccharides, such as cellulose, starch, agarose, dextran (soluble or insoluble), carrageenin, alginate and chitin; vinyl polymers; polyamines; proteins; polyamides and polyurethane.

The cross-linking polymerization process required for entrapping the enzyme-polymer-complex or enzyme-monomer-complex first prepared and the microorganism can be effected in various ways, depending on the polymer used, for example by temperature changes (e.g. in respect of carrageenin), by changing the ion-composition in the medium (e.g. in the case of alginate), by photometric processes (e.g. in the case of urethane) and by adding a suitable polymerization catalyst (e.g. in the case of polyacrylamide). Conveniently, the prepared polymer bodies with the covalently bound enzyme and the physically entrapped microorganism have the form of small beads with a diameter of some tenths of a millimeter or some few millimeters. It will be understood, of course, that bodies of other shapes and/or sizes can be used.

Practically all types of microorganisms can be used according to the invention, such as algae, bacteria, bacteriophage, fungi, viruses and antisera, protozoes and yeast. Examples of such microorganisms are found in the following publications: The American Type Culture Collection, Catalogue of Strains I, 1978, Stainer, R. Y., Adelberg, E. A., and Ingraham, J. L.; and "General Microbiology", Fourth Edition, 1979. The Macmillan Press Ltd.

The invention can also be applied with practically all types of enzymes, such as oxidoreductases, transferases, hydrolases, lyases, isomerases and ligases. Enzymes belonging to these six groups are found recited in the publication entitled Enzyme Nomenclature, Recommendations (1978) of the Nomenclature Committee of the International Union of Biochemistry; published for the International Union of Biochemistry by Academic Press (AP), Inc.

The invention has primarily been tested for the manufacture of catalysts for converting cellobiose to ethanol via glucose in accordance with the reaction sequences given in the introduction, in which catalyst the covalently bound enzyme was $\beta$-glucosidase and the physically entrapped microorganism was Bakers yeast (*Saccharomyces cerivisiae*), and the polymer material was alginate.

EXAMPLE 1

100 mg of sodium alginate were suspended in 2 ml of distilled water. 32 mg of N-hydroxysuccinimide and 28 mg EDC dissolved in 1 ml of distilled water were added in order to activate the alginate. Activation of the alginate took place for 15 minutes at room temperature. 15 mg of β-glucosidase dissolved in 1 ml water were then added. Coupling between alginate and enzyme was allowed to continue overnight in a cold environment. On the following day, a suspension of a further 200 mg of alginate in 6 ml of distilled water were mixed with the obtained alginate-β-glucosidase-complex, to obtain a final volume of 10 ml. 500 mg of Bakers yeast suspended in 5 ml of 0.1 M acetate buffer, pH=4.9, were then added to the solution, so that a suspension volume of about 15 ml was obtained. With the aid of this suspension, a calcium alginate gel was prepared, by slowly dripping the suspension into a solution of 0.1 M $CaCl_2$ in a 0.1 M acetate buffer, pH=4.9, whereby small beads of alginate gel with a mean diameter of about 2 mm were obtained. The gel beads were kept in the calcium chloride solution for at least three hours, during which time the cross-linking of the alginate gel took place, whereafter the beads were removed and stored in an acetate buffer containing 0.01 M $CaCl_2$. About 7.4 g (wet-weight) of gel were obtained from a suspension of about 15 ml of alginate sol.

Alginate beads produced in this way and containing covalently bound β-glucosidase and physically entrapped Bakers yeast were used for the manufacture of ethanol, with 5% cellobiose as the starting material. The alginate beads were arranged in a column. The volume of the column was 7.5 ml and the column contained 5.25 grams (wet weight) of alginate beads and was operated at a temperature of 22° C. The conversion of cellobiose to ethanol approached close to the theoretical value after three days, whereafter the ethanol production reached a steady state of 1.5% (weight/volume), corresponding to about 60% of the theoretic yield. The activity of the alginate beads was found to be stable for at least four weeks, at said working temperature. The course followed by the process is illustrated by the lower curve in the accompanying drawing.

Alginate beads produced in the manner described, but containing three times as much enzyme were tested in a similar manner, the result obtained being illustrated by the upper curve in the drawing. With the alginate beads of higher enzyme activity, the yield was thus raised from 60% to 80% of the theoretic value. The activity of catalysts formed by the alginate beads was also in this case found to be stable for at least four weeks.

In a manner similar to that in Example 1, catalysts comprising beads of calcium alginate gel were also prepared, in which the covalently bound enzyme was β-galactosidase, amylase, a mixture of endo- and exo-glucanases and β-glucosidase, respectively. β-galactosidase decomposes the lactose in, for example, whey into glucose, and hence the alginate beads containing this enzyme could be used in the manufacture of ethanol from whey. The enzyme amylase decomposes starch to glucose, and hence alginate beads containing this enzyme could be used in the manufacture of ethanol from starch. The cellulolytic enzymes endoglucanases, exoglucanases and β-glucosidases together break down cellulose to glucose, in accordance with reaction processes recited in the introduction, and hence alginate beads containing a mixture of these enzymes could be used in the manufacture of ethanol from cellulose hydrolyzate.

When the enzyme bound to the alginate beads produced in the manner described in Example I is xylosisomerase, there is obtained a catalyst which can be used in the manufacture of ethanol from xylose, via xylulose as an intermediate product.

By using Penicillium sp as microorganism and acylase as enzyme it is possible to manufacture, in the manner described in Example 1, a catalyst which can be used for preparing 6-APA in accordance with the reaction formula given in the introduction.

Although the invention has been exemplified in detail in the aforegoing, primarily with respect to catalysts comprising polymeric alginate alginate beads which contain physically entrapped Bakers yeast as the microorganism and various, covalently bound enzymes for the manufacture of ethanol from various substrate substances, it will be understood that many other catalysts according to the invention can be prepared from many kinds of polymeric material other than those described, with the use of different enzymes and microorganisms in accordance with the exemplifications given in the aforegoing, for carrying out many different biochemical conversion reactions.

We claim:

1. A method of preparing a catalyst for biochemical conversion reactions, which require the presence of at least one enzyme and at least one microorganism, wherein there is added to a polymer or monomer in solution or suspension at least one enzyme, subsequent to previously activating suitable groups of the enzyme or of the polymer or monomer, so that when the polymer, or monomer, and the enzyme are brought together the enzyme is bound to the molecules of said polymer, or monomer, by covalent bonds, whereafter the polymer, or monomer, with the enzyme covalently bound thereto is mixed in solution or suspension with at least one microorganism and a polymer, or monomer, capable of being cross-linked, whereafter the mixture thus obtained is subjected to a cross-linking polymerization process so as to obtain solid bodies of polymer containing the enzyme covalently bound to the polymer material, and the microorganism entrapped in the three-dimensional cross-linked structure of said bodies.

2. A method as claimed in claim 1, wherein for the purpose of establishing the covalent bonds between said enzyme and said polymer, or monomer, there are used hydroxyl groups, carboxyl groups, phenyl groups, tyrosyl groups, amino groups or thiol groups of the enzyme or of the polymer or monomer.

3. A method as claimed in claim 1, wherein said covalent bonds are established by activating selected groups on the polymer or monomer.

4. A method as claimed in claim 1, wherein the polymer or monomer used to obtain the final cross-linked polymerized three-dimensional structure is of the same kind as the polymer or monomer used for the covalent bonding of the enzyme.

5. A method as claimed in claim 1, wherein the polymer material of the solid bodies is selected from the group consisting of polysaccharides, vinyl polymers, polyamino acids, proteins, polyamides and polyurethanes.

6. A method as claimed in claim 5, wherein the polysaccharide is cellulose, starch, agarose, dextran, carrageenan, alginate or chitin.

7. A method as claimed in claim 1, wherein the enzyme is an oxidoreductase, a transferase, hydrolase, lyase, isomerase or ligase.

8. A method as claimed in claim 1, wherein the microorganism comprises algae, bacteria, fungii, protozoa or yeast.

9. A method as claimed in claim 1, for preparing a catalyst for the production of ethanol by means of a biochemical conversion process, wherein said enzyme is selected from the group consisting of B-glucosidase, B-galactosidase, amylase, xylosisomerase and a mixture of endoglucanase, exoglucanase and B-glucosidase, and said polymer to which said enzyme is bound covalently is sodium alginate in a suspension;

a suspension is prepared from the resulting sodium alginate-enzyme-complex, additional sodium aliginate and Bakers yeast; and said cross-linking is carried out by introducing said suspension into a solution of calcium chloride so as to produce beads of cross-linked calcium alginate gel containing covalently bound enzyme and entrapped Bakers yeast.

* * * * *